United States Patent [19]

Shirakura et al.

[11]  4,426,376

[45]  Jan. 17, 1984

[54] NEUTRALIZER FOR PERMANENT WAVE

[75] Inventors: Sachiko Shirakura, Shinbashi; Hiroo Namiki, Hanno, both of Japan

[73] Assignee: Helene Curtis Industries, Inc., Chicago, Ill.

[21] Appl. No.: 343,528

[22] Filed: Jan. 28, 1982

[51] Int. Cl.³ .......................... A61K 7/09; A61K 7/11; C08B 37/02

[52] U.S. Cl. ........................................ 424/71; 424/72; 536/51; 536/112

[58] Field of Search .................... 424/71, 72; 536/112, 536/51

[56] References Cited

U.S. PATENT DOCUMENTS 3,837,349  9/1974  Jedzinak et al. ...................... 424/71
4,318,901  3/1982  Ishida et al. ........................... 424/72

FOREIGN PATENT DOCUMENTS 801990  9/1958  United Kingdom .................. 424/71

Primary Examiner—Jerome D. Goldberg
Assistant Examiner—F. Abramson
Attorney, Agent, or Firm—Dressler, Goldsmith, Shore, Sutker & Milnamow, Ltd.

[57]  ABSTRACT

A neutralizer for permanent waving of hair is disclosed. The neutralizer contains (A) 0.5–16% (w/v) of an oxidizing agent capable of reforming ruptured disulfide bonds in reduced hair and (B) 0.1–5% (w/v) of a cationic dextran derivative or its salt as indispensible components, and has a pH value range of from about 2 to about 10.5.

9 Claims, No Drawings

NEUTRALIZER FOR PERMANENT WAVE

BACKGROUND OF THE INVENTION

The present invention relates to neutralizers for permanent waves. Furthermore, it relates to those neutralizers for permanent waves which contain oxidizing agents, such as hydrogen peroxide, alkali metal bromates or alkali metal perborates, that are capable of reforming ruptured disulfide bonds in reduced hair formed during the permanent waving process.

In general, the perming process by reagents for permanent wave consists of cleaving the disulfide bonds of keratin in the hair by mercapto compounds, such as thioglycolates or cysteine, and subsequently forming new disulfide bonds by an oxidizing agent, such as a bromate, or hydrogen peroxide or others.

However, the conventional neutralizers have had disadvantages such as poor wave durability, unsatisfactory touch of the permed hair and fear of damaging hair. The present invention was carried out in order to improve these defects.

SUMMARY OF THE INVENTION

The present invention relates to a neutralizer for permanent hair waving. The neutralizer comprises about 0.5 to about 16% (w/v) of (A) and about 0.1 to about 5% (w/v) of (B) as indispensable components. As used herein, (A) denotes an oxidizing agent capable of reforming ruptured disulfide bonds in reduced hair, and (B) denotes a cationic dextran derivative or its salt. The neutralizer has a pH value in the range of from about 2 to about 10.5.

DETAILED DESCRIPTION OF THE INVENTION

In accordance with the present invention, a cationic dextran derivative is compounded into the neutralizer composition for application to the hair in the usual manner.

Compounding the cationic dextran derivatives into the neutralizer for permanent wave permits the reagent to achieve excellent improvement in affinity with the hair, flexibility and water-perservability of the formed coatings and touch of the permed hair. These effects are most noticeable when the hair is dried.

The cationic dextran derivatives and their salts (B) are represented by the following formula (1)

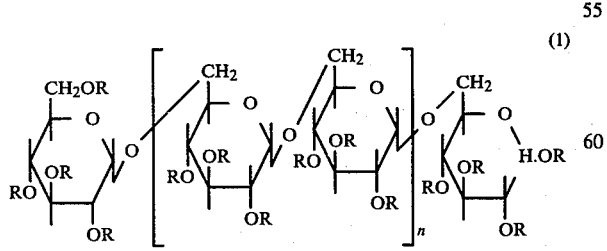

wherein R are members selected from a group consisting of hydrogens and quaternary nitrogen-containing groups of the following formula (2)

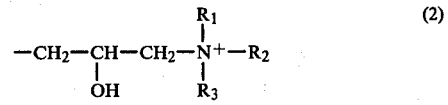

and at least one R of formula (1) is of the group containing a quaternary nitrogen represented by the above formula (2), wherein $R_1$, $R_2$ and $R_3$ are lower-alkyl groups respectively, and n is a positive number having a value between 1–8000, and preferably from about 50 to about 200, and more preferably, n has a value of about 75 to about 175. These cationic dextran derivatives are readily soluble in water and have excellent properties in such items as antistatic effect, complexing ability with both anionic and amphoteric surface active reagents, colloid-protective effect and coatings-formation ability.

The cationic dextran derivatives useful herein can be produced, for example, by the reaction of dextran with a salt of cation of the following formula (3)

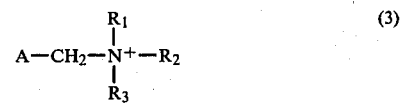

wherein $R_1$, $R_2$ and $R_3$ are lower-alkyl groups respectively and A is

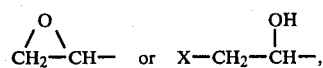

wherein X is a halogen.

Typical examples of the salts of formula (3) cations are glycidyl tri-(lower alkyl) ammonium salts and 3-halo-2 hydroxypropyl-tri-(lower alkyl) ammonium salts.

In the formula representing the cation (3), the lower alkyl group is preferably an alkyl group having 1 to 4 carbon atoms, and examples of halogen are preferably chloro and bromo.

Examples of the salts of formula (3) cations include the following:
glycidyl trimethyl ammonium salts,
glycidyl triethyl ammonium salts,
glycidyl tripropyl ammonium salts,
glycidyl ethyldimethyl ammonium salts,
glycidyl diethylmethyl ammonium salts,
glycidyl tri-n-butyl ammonium salts,
glycidyl tri-iso-butyl ammonium salts,
3-chloro-2-hydroxypropyltrimethyl ammonium salts,
3-chloro-2-hydroxypropyltriethyl ammonium salts,
3-chloro-2-hydroxypropyltri-n-butyl ammonium salts,
3-chloro-2-hydroxypropyltri-iso-butyl ammonium salts,
3-bromo-2-hydroxypropyltrimethyl ammonium salts,
3-bromo-2-hydroxypropyltriethyl ammonium salts,
3-bromo-2-hydroxypropyltri-n-butyl ammonium salts, and
3-bromo-2-hydroxypropyltri-iso-butyl ammonium salts.

The aforementioned salts can be either mineral salts and organic acid salts of the above cations. Examples of acids for forming the above inorganic or organic salts are hydrochloric acid, phosphoric acid, sulfuric acid, nitric acid, acetic acid and hydrobromic acid.

The reaction of dextran with the salt of the cation of formula (3) can be carried out, for example, by contacting dextran with the salt in an aqueous medium. Specifically, the reaction can be carried out by dissolving or suspending dextran in an aqueous medium such as water or a mixture of water and an alcohol in the presence of an alkaline catalyst and then adding the salt of the formula (3) cation. Examples of the alkaline catalyst used in the reaction are hydroxides and carbonates of alkali metals such as sodium hydroxide, potassium hydroxide and sodium carbonate, and hydroxides of alkaline earth metals such as calcium hydroxide.

The reaction temperature is, for example, from about 0° C. to about 80° C. to 100° C., preferably from room temperature to about 60° to 70° C. The reaction time can be suitably selected, and is, for example, about 20 minutes to about 24 hours. After the reaction, the product is separated and purified as required by such means as filtration, dialysis and reprecipitation to give a cationized dextran derivative.

The cationic dextran (B) can be present in an amount of about 0.1 to about 5% (w/v) of the neutralizer. More preferably, it is present at about 1 to about 2% (w/v).

In addition to the above cationic dextran (B), a second indispensible component is an oxidizing agent capable of reforming ruptured disulfide bonds in reduced hair (A). Examples of such oxidizing agents include hydrogen peroxide, alkali metal perborates, such as sodium perborate, and alkali metal bromates, such as potassium bromate.

The neutralizer compositions can be at pH values that range from about 2 to about 10.5, with the pH value of a particular neutralizer being largely dependent upon the oxidizing agent (A) selected. For example, when alkali metal bromates or hydrogen peroxide are used, the neutralizer pH value is not higher than about 8. The pH value is more preferably from about 5 to 6 for bromates, and when hydrogen peroxide is utilized, the pH value is more preferably from about 3.5 to 4.0. Alkali metal perborates are preferably used at pH values higher than about 8, and more preferably at about pH 10.

The indispensible oxidizing agent (A) is preferably used in an amount of about 0.5–16% (w/v) of the composition, and for oxidizing agents (A), other than hydrogen peroxide, the amount is more preferably about 3.5–16% (w/v). When hydrogen peroxide is the oxidizing agent (A), it is more preferably present at about 1 to about 2% (w/v).

SPECIFIC EMBODIMENTS

The following examples will serve to illustrate the present invention.

| Waving lotion [A] | |
|---|---|
| Ammonium thioglycolate (50% aqueous solution as thioglycolic acid) | 13.0 g |
| Concentrated aqueous ammonia | 3.5 g |
| Polyoxyethylene oleyl ether (polymerized with 20 units of ethylene oxide) | 0.5 g |
| Perfume | a slight amount |
| Coloring agent | a slight amount |
| Distilled water | remaining amount |
| Total Amount | 100.0 g |
| pH 9.4 (25° C.) | |

The above waving lotion [A] was used in the tests for wave durability and hair strength.

| [B] | |
|---|---|
| Ammonium thioglycolate (50% aqueous solution as thioglycolic acid) | 11.0 g |
| Concentrated aqueous ammonia | 1.0 g |
| Sodium hydroxide 20% aqueous solution | 0.5 g |
| Ammonium bicarbonate | 2.5 g |
| Polyoxyethylene lanolin (polymerized with 80 units of ethylene oxide) | 1.5 g |
| Polyoxyethylene oleyl ether (polymerized with 20 units of ethylene oxide) | 0.5 g |
| Perfume | a slight amount |
| Coloring agent | a slight amount |
| Distilled water | remaining amount |
| Total amount | 100.0 g |
| pH 8.6 (25° C.) | |

The above waving lotion [B] was used in the tests for change of the external condition of the hair and sensory tests.

A series of neutralizer compositions representing embodiments of this invention (Examples 1–4) and representing typical prior art compositions (Comparative Examples 1 and 2) were prepared in accordance with formulations shown in Table I.

TABLE 1

| Example | 1 | 2 | 3 | 4 | Comparative Ex. 1 | Comparative Ex. 2 |
|---|---|---|---|---|---|---|
| Sodium Bromate | 10.0 g | 10.0 g | 10.0 g | 10.0 g | 10.0 g | 10.0 g |
| Polyether (1) | 1.0 g | 1.0 g | 1.0 g | 1.0 g | 1.0 g | 1.0 g |
| Cationic Dextran A (2) | 1.0 g | 2.0 g | — | — | — | — |
| Cationic Dextran B (3) | — | — | 1.0 g | 2.0 g | — | — |
| Cationated Cellulose (4) | — | — | — | — | 2.0 g | — |
| Phosphoric Acid | to pH 5.5 | to pH 5.5 | to pH 5.5 | to pH 5.5 | to pH 5.5 | to pH 5.5 |
| Distilled Water | to 100 g | to 100 g | to 100 g | to 100 g | to 100 g | to 100 g |

(1) polyoxyethylene octyl phenyl ether (polymerized with 10 units of ethylene oxide)
(2) (2-hydroxy-3-trimethylpropyl ammonium) dextran chloride; n = about 110
(3) (2-hydroxy-3-triethylpropyl ammonium) dextran chloride; n = about 110
(4) the compound in which glycidyl-trimethylammonium chloride was combined with hydroxyethyl cellulose by forming ether bonds To prepare test hair for treatment, female virgin hair 20 cm long was washed for 2 minutes with 1% solution of sodium lauryl sulfate, then rinsed with tap water for 5 minutes and air dried.

WAVE DURABILITY TESTS

In each test, a bundle of 20 hairs was wound around the mandrel of a Kirby device. Then, 20 ml of the waving lotion was applied to the hair and allowed to stand for 15 minutes at about 25° C. The hair was rinsed for 2 minutes with tap water and the water was thoroughly removed. After that, 20 ml of the neutralizer was applied to the hair and allowed to stand for 15 minutes at 25° C. The hair was rinsed for 2 minutes with tap water and then removed from the device. The length of 6 waves of the curled hair was measured and represented by $l_o$.

Then the curled hair was soaked in 100 ml of warm water (about 40° C.) for 24 hours and taken out from the warm water. The length of 6 waves of the curled hair was measured and represented by 1. Wave durability was calculated with the following equation.

$$100 - \left( \frac{1 - l_o}{l_o} \times 100 \right) = \text{wave durability (\%)}$$

When the foregoing tests were run using as the neutralizers the compositions of Example 2 and comparative Examples 1 and 2, the results obtained are shown in Table II

TABLE II

| Composition | Wave durability |
|---|---|
| Example 2 | 90.29 |
| Comparative Example 1 | 86.49 |
| Comparative Example 2 | 85.48 |

The above results show that compounding cationic dextran derivatives improve wave durability.

MEASUREMENT OF HAIR STRENGTH

In each test, a bundle was made with 1 g of the test hair and wound around a rod for permanent wave. Then 20 ml of the waving lotion was applied to the hair, allowing to stand for 30 minutes at about 25° C. and rinsed with tap water for 2 minutes. After the water was thoroughly removed, 20 ml of the neutralizer was applied to it, allowed to stand for 30 minutes at about 25° C. and rinsed with tap water for 2 minutes. The hair was unwound from the rod and air-dried at room temperature. This hair was placed over silica gel in a desiccator for 24 hours and then the strength was measured by a tensile tester UTM-11 type (Toyo Bowledwin Co., Ltd.) at 20±1° C. and 40±2% RH.

In order to evaluate one sample, the mean value of data measured for 30 hairs was obtained.

When the neutralizers of Example 2 and Comparative Example 2 were compared after the foregoing treatment with each other and with untreated hair the results obtained are shown in Table III.

TABLE III

| | 2% Ext. (kg/cm$^2$)[1] | 15% Ext (kg/cm$^2$)[2] | Breaking stress (kg/cm$^2$)[3] | Elongation ratio (%)[4] |
|---|---|---|---|---|
| Example 2 | 16.98 | 22.20 | 34.20 | 41.18 |
| Comparative Example 2 | 14.48 | 17.26 | 26.42 | 47.95 |
| Untreated hair | 17.35 | 22.77 | 34.92 | 39.79 |

[1]Stress per a unit area of a hair when elongated by 2%.
[2]Stress per a unit area of a hair when elongated by 15%.
[3]Stress per a unit area of a hair at the breaking point.
[4]Elongation ratio of a hair at the breaking point.

After the use of the neutralizer of Example 2, lowering of stresses was small and the difference of elongation ratio was also small, when compared with that of untreated hair. However, when the neutralizer of Comparative Example 2 was used, the lowering of stresses was obviously large and the increase in elongation ratio was several times as large as the increase produced by the Example 2 composition. Therefore, it is clear that compounding cationic dextran derivatives prevents the hair from being damaged.

CHANGES OF THE EXTERNAL CONDITIONS OF THE HAIR

Hair bundles each made of 1 g of the test hair were wound around rods of 8.5 mm diameter for permanent wave. In that condition, 20 ml of the waving lotion was applied to it and allowed to stand for 15 minutes at about 25° C. The hair was rinsed with tap water for 2 minutes and the water was thoroughly removed. Then, the neutralizers of Example 2 and of Comparative Examples 1 and 2 were applied to separate bundles and allowed to stand for 15 minutes at about 25° C. The hair was rinsed with tap water for 2 minutes, unwound from the rods, air dried at room temperature and combed twenty times with a comb. One hair bundle was left untreated as a control.

The same treatment was repeated twice, namely, each hair bundle, except the control, was treated 3 times. The external condition of this treated hair was observed by a scanning electron microscope (HSM-2B Hitachi Co., Ltd.) at a power of 800. The results are shown in Table IV.

TABLE IV

| No. 1 | Untreated hair | The cuticle was uniform. |
|---|---|---|
| No. 2 | Example 2 | The cuticle was as uniform as that of untreated hair |
| No. 3 | Comparative Example 1 | A part of the cuticle was peeled off. |
| No. 4 | Comparative Example 2 | Minute unevenness was observed on the edge. |

SENSORY TESTS

The finished conditions of permanent-wave treatment for 10 women between 18-25 years of age were sensually tested by 5 panelists.

The hair of the women to be treated was parted in the middle, wound with applying 40 ml of the waving lotion by the ordinary method and 40 ml of the waving lotion was applied uniformly to the whole hair again after the winding operation was completed. The hair was capped and allowed to stand for about 15 minutes, rinsed thoroughly with tepid water and dried by removing the water with a towel. Then the neutralizer of Example 2 was applied to one half of the hair and the neutralizer of Comparative Example 1 was applied to the other half; and both halves were allowed to stand for about 15 minutes. The hair was unwound from the rods, rinsed thoroughly with tepid water and dried with a towel. Ease of combing, touch and oiliness of the hair were evaluated after the hair was dried with a dryer. The results are shown in Table V.

TABLE V

| | Ease of Combing | Touch | Sheen |
|---|---|---|---|
| Example 2 | smooth | soft | good |
| Comparative Example 1 | Ends of hair tangled | a little stiff | good |

EXAMPLES OF PREPARATION OF CATIONIC DEXTRAN

A typical cationic dextran useful in the neutralizers of this invention can be prepared as follows.

Dextran (81 grams) having an average molecular weight of about 59,000 and water (100 milliliters) are placed into a reaction vessel. Thereafter, 200 milliliters of a 40% by weight aqueous solution of sodium hydroxide are added and the resulting mixture is stirred for 10 minutes. Then, 700 milliliters of an aqueous solution containing glycidyl trimethyl ammonium chloride (387 grams) are added. The resulting admixture is heated to a temperature of 60° C. and is allowed to react for 4 hours, with agitation. Upon cooling to about room temperature, the reaction mixture is neutralized with acetic acid, and is dialized against flowing water for 24 hours. The dialyzate is lyophilized to yield 135 grams of a white powder of cationized dextran chloride being soluble in water and ethanol and having an n value of about 181.

Another typical cationic dextran useful herein can be prepared as follows.

Dextran (105 grams) having an average molecular weight of about 34,000 is dissolved in water (125 milliliters). Sodium hydroxide (40 milliliters of a 48.5 percent by weight aqueous solution) is added along with 3-chloro-2-hydroxypropyltrimethyl ammonium chloride (190 milliliters of an aqueous solution containing 110 grams). The solution is heated to 60° C. and is allowed to react for 3 hours. On cooling to about room temperature, the reaction mixture is neutralized with hydrochloric acid and the cationic dextran is precipitated four times from aqueous solution using acetone. Spray drying of the precipitates yields 140 grams of white powder of cationized dextran chloride which is soluble in water and 60 percent ethanol and has an n value of about 104.

The invention is defined by the claims which follow.

We claim:

1. A neutralizer for permanent wave processing comprising 0.5–16% (w/v) of (A) and 0.1–5% (w/v) of B as indispensible components, where (A) denotes an oxidizing agent capable of reforming ruptured disulfide bonds in reduced hair and (B) denotes a cationic dextran derivative or its salt represented by formula (1)

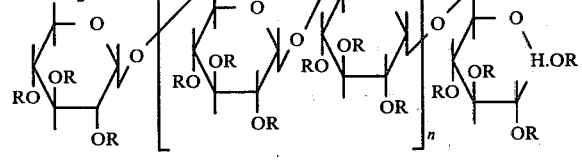

wherein R is selected from the group consisting of hydrogen and a quaternary nitrogen-containing group represented by formula (2)

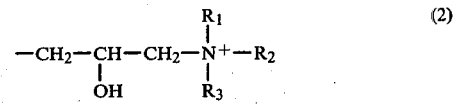

at least one R of formula (1) contains a quaternary nitrogen represented by formula (2), wherein $R_1$, $R_2$ and $R_3$, are lower-alkyl, and n is a positive number having a value between 1–8000.

2. A neutralizer for permanent wave as set forth in claim 1, wherein the component (A) is selected from the group consisting of alkali metal bromates, hydrogen peroxide and alkali metal perborates.

3. A neutralizer for permanent wave as set forth in claim 1 wherein the component (A) is present in an amount from about 3.5 to about 16% (w/v).

4. A neutralizer for permanent wave as set forth in claim 1 wherein the pH is not higher than about 8.

5. A neutralizer for permanent wave as set forth in claim 1 wherein the component (A) is hydrogen peroxide present in an amount from about 1 to about 2% (w/v) and the pH is from about 3.5 to 4.0.

6. A neutralizer for permanent wave as set forth in claim 1 wherein the component (A) is an alkali metal bromate.

7. A neutralizer for permanent wave as set forth in claim 1 wherein the component (A) is an alkali metal perborate and the pH is about 10.

8. A neutralizer for permanent wave as set forth in claim 7 wherein the value of n is about 50 to about 200.

9. A method for neutralizing reduced hair that has been reduced with a mercaptan reducing agent applied to the hair for permanent waving which comprises applying to said reduced hair, after rinsing, an effective amount of the neutralizer of claim 1.

* * * * *